(12) United States Patent
Crass et al.

(10) Patent No.: US 7,657,443 B2
(45) Date of Patent: Feb. 2, 2010

(54) INTRAVENOUS MEDICATION HARM INDEX SYSTEM

(75) Inventors: Richard E. Crass, San Diego, CA (US); Timothy W. Vanderveen, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 1072 days.

(21) Appl. No.: 10/741,042

(22) Filed: Dec. 19, 2003

(65) Prior Publication Data

US 2005/0224083 A1    Oct. 13, 2005

(51) Int. Cl.
    *G06Q 50/00*    (2006.01)
(52) U.S. Cl. .......................................... 705/2
(58) Field of Classification Search ............. 705/2
    See application file for complete search history.

(56) References Cited

U.S. PATENT DOCUMENTS

| | | | |
|---|---|---|---|
| 5,463,768 A | | 10/1995 | Cuddihy et al. |
| 5,659,731 A * | | 8/1997 | Gustafson .................. 707/4 |
| 5,681,285 A * | | 10/1997 | Ford et al. .................. 604/151 |
| 5,781,442 A | | 7/1998 | Engleson et al. |
| 5,845,255 A | | 12/1998 | Mayaud |
| 6,000,828 A | | 12/1999 | Leet |
| 6,108,685 A | | 8/2000 | Kutzik et al. |
| 6,219,674 B1 | | 4/2001 | Classen |
| 6,269,340 B1 * | | 7/2001 | Ford et al. .................. 705/3 |
| 6,598,179 B1 * | | 7/2003 | Chirashnya et al. ............ 714/37 |
| 6,788,965 B2 * | | 9/2004 | Ruchti et al. ................ 600/316 |
| 7,551,078 B2 * | | 6/2009 | Carlson et al. .......... 340/539.12 |
| 2001/0020240 A1 | | 9/2001 | Classen |
| 2002/0077852 A1 * | | 6/2002 | Ford et al. ..................... 705/2 |
| 2002/0077865 A1 | | 6/2002 | Sullivan |
| 2002/0083080 A1 | | 6/2002 | Classen |
| 2002/0165845 A1 | | 11/2002 | Gogolak |
| 2002/0165852 A1 | | 11/2002 | Gogolak |
| 2002/0165853 A1 | | 11/2002 | Gogolak |

(Continued)

OTHER PUBLICATIONS

"New Medication Errors Taxonomy Released" Mar. 15, 1999, "NCC MERP Taxonomy of Medication Errors" 1998, "NCC MERP Index for Categorizing Medication Errors" 2001, and "Medication Errors Council Revises and Expands Index for Categorizing Errors" Jun. 12, 2001 by the National Coordinating Council for Medication Error Reporting and Prevention (NCC MERP).*

Medical Devices & Surgical Technology Week, "Medication Safety; IV medication harm index unveiled at conference", Atlanta: Dec. 21, 2003. p. 108.*

(Continued)

*Primary Examiner*—C. Luke Gilligan
*Assistant Examiner*—Robert Sorey
(74) *Attorney, Agent, or Firm*—McDermott Will & Emery LLP

(57) ABSTRACT

A system and method for assessing the severity of medication errors associated with intravenous administration is provided. A harm index database includes harm index values for various parameters of medication administration. A medication administration device may access this database and assess the overall harm index for particular errors in order to provide appropriate alerts based on the severity of the error. Further, assessment of the harm index value may be used retrospectively to provide reports of event logs that include an overall harm index value associated with each alert.

16 Claims, 6 Drawing Sheets

| | | | | | | | Initial Programming | | | Harm Index | Subsequent Programming | | | |
|---|---|---|---|---|---|---|---|---|---|---|---|---|---|---|
| Bolus Doses shown in *Bold Italic* | | | | | | | | | | | | | University Hospital | |
| Date | Time (hrs) | Profile | Pt. Weight | Drug Infused | | | Programmed Dose | GR Limit | Times the Limit | | Final Dose OR Other | Times Intended Dose | POC Unit | |
| 7/5/2003 | 16:40:43 | NICU | 2.5 kg | DOPamine 148 mg / 100 mL | | | 78.93 mcg/kg/min | 20 | 3.95 | 9 | 7.89 mcg/kg/min | 10 | 4021746 | |
| 7/6/2003 | 9:55:00 | MICU | | fentanyl 2500 mcg / 250 mL | | | 2000 mcg/hr | 400 | 5 | 13 | 20 mcg/hr | 100 | 4022291 | |
| 7/22/2003 | 11:03:00 | PICU | 3.0 kg | DOPamine 36 mg / 100 mL | | | 11 mcg/kg/min | 10 | 1.1 | 4.2 | 10 mcg/kg/min | 1.1 | 4020211 | |
| 6/1/2003 | 8:49:00 | ADULT | | pantoprazole 80 mg / 250 mL | | | 16 mg/hr | 8 | 2 | 4.5 | 8 mg / hr | 2 | 4021738 | |
| 5/17/2003 | 16:26:00 | Anesthesia | 70 kg | insulin 100 unit / 100 mL | | | 0.90 unit/kg/hr | 0.2 | 4.5 | 12 | Cancelled Infusion | | 4020287 | |
| 8/6/2003 | 20:09:00 | Hematology/Oncoloty | 15.2 kg | midazolam 1 mg / 1 mL | | | 1.32 kg/kg/hr | 0.2 | 6.58 | 12.2 | Cancelled Infusion | | 4021369 | |
| 7/9/2003 | 5:54:48 | MICU | | heparin 25000 unit / 250 mL | | | 10000 unit/hr | 3000 | 3.33 | 13 | 1000 unit/hr | 10 | 4013913 | |
| 7/20/2003 | 2:01:14 | MICU | | heparin 25000 unit / 250 mL | | | 7450 unit/hr | 3000 | 2.48 | 10 | 1450 unit/hr | 5.14 | 4021746 | |

U.S. PATENT DOCUMENTS

| | | |
|---|---|---|
| 2002/0169636 A1 | 11/2002 | Eggers et al. |
| 2002/0183965 A1 | 12/2002 | Gogolak |
| 2002/0188465 A1 | 12/2002 | Gogolak et al. |
| 2003/0046110 A1 | 3/2003 | Gogolak |
| 2003/0060688 A1 | 3/2003 | Ciarniello et al. |
| 2004/0073329 A1* | 4/2004 | Engleson et al. ............ 700/131 |
| 2004/0121767 A1* | 6/2004 | Simpson et al. .......... 455/426.1 |
| 2004/0127337 A1* | 7/2004 | Nashner ..................... 482/100 |
| 2004/0193325 A1* | 9/2004 | Bonderud et al. ........... 700/282 |
| 2005/0015278 A1* | 1/2005 | Ghouri ......................... 705/2 |

OTHER PUBLICATIONS

James G. Anderson, Ph.D., Stephen J. Jay, MD, Marilyn Anderson, BA, Thaddeus J. Hunt, BA; *Evaluating the Capability of Information Technology to Prevent Adverse Drug Events: A Computer Simulation Approach*; Journal of the American Medical Information Association, vol. 9, No. 5, Sep./Oct. 2002.

PCT International Search Report for International Application No. PCT/US2004/42510 mailed Sep. 27, 2007.

\* cited by examiner

400

| DRUG TYPE | Dose (times maximum limit) /score — 404 | | |
|---|---|---|---|
| | Low | Moderate | High |
| Low Risk | (1 – 4) 1.5 | (4.1 – 9.9) 2 | (>10) 3 |
| Medium Risk | (1 – 2) 2 | (2.1 – 4.9) 4 | (>5) 6 |
| High Risk | (1 – 1.5) 3 | (1.6 – 2.4) 6 | (>2.5) 9 |

FIG. 4A

| Level of Care | Description | Score |
|---|---|---|
| General | Medical, Surgical, Other | 1 |
| Intermediate | Non-ICU beds with telemetry | 1.2 |
| Adult ICU | — | 2 |
| PICU or NICU | Pediatric ICU, Neonatal ICU | 3 |

FIG. 4B

| Detectability | Score |
|---|---|
| Likely | 1 |
| Unlikely | 2 |

FIG. 4C

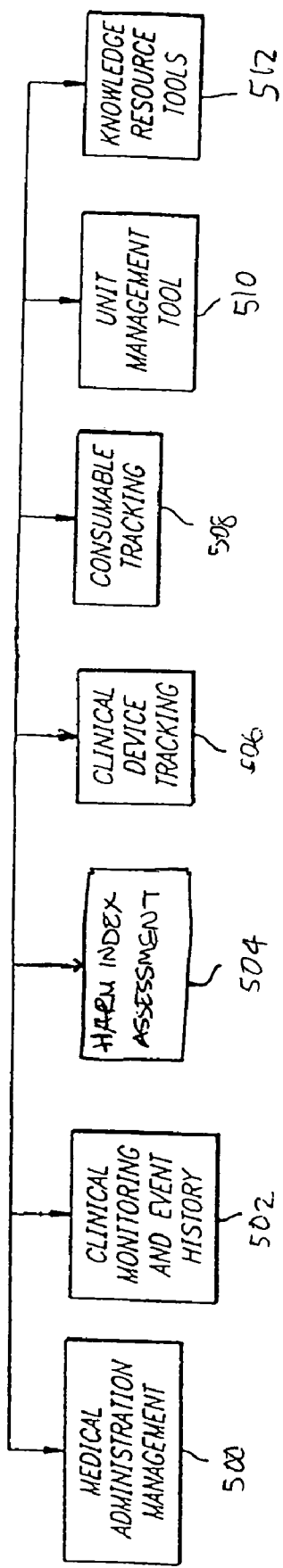

Bolus Doses shown in *Bold Italic*

University Hospital

| Date | Time (hrs) | Profile | Pt. Weight | Drug Infused | Initial Programming | | | Harm Index | Subsequent Programming | | POC Unit |
|---|---|---|---|---|---|---|---|---|---|---|---|
| | | | | | Programmed Dose | GR Limit | Times the Limit | | Final Dose OR Other | Times Intended Dose | |
| *7/5/2003* | *18:40:43* | *NICU* | *2.5 kg* | *DOPamine 148 mg / 100 mL* | *78.93 mcg/kg/min* | *20* | *3.95* | *9* | *7.89 mcg/kg/min* | *10* | *4021746* |
| 7/6/2003 | 9:55:00 | MICU | | fentanyl 2500 mcg / 250 mL | 2000 mcg/hr | 400 | 5 | 13 | 20 mcg/hr | 100 | 4022291 |
| *7/22/2003* | *11:03:00* | *PICU* | *3.0 kg* | *DOPamine 36 mg / 100 mL* | *11 mcg/kg/min* | *10* | *1.1* | *4.2* | *10 mcg/kg/min* | *1.1* | *4020201* |
| 6/1/2003 | 8:49:00 | ADULT | | pantoprazole 80 mg / 250 mL | 16 mg/hr | 8 | 2 | 4.5 | 8 mg / hr | 2 | 4021738 |
| *5/17/2003* | *16:26:00* | *Anesthesia* | *7.0 kg* | *insulin 100 unit / 100 mL* | *0.90 unit/kg/hr* | *0.2* | *4.5* | *12.2* | *Cancelled Infusion* | | *4020287* |
| 8/6/2003 | 20:09:00 | Hematology/Oncoloty | 15.2 kg | midazolam 1 mg / 1 mL | 1.32 mg/kg/hr | 0.2 | 6.58 | 12.2 | Cancelled Infusion | | 4021369 |
| *7/9/2003* | *5:54:43* | *MICU* | | *heparin 25000 unit / 250 mL* | *10000 unit/hr* | *3000* | *3.33* | *13* | *1000 unit/hr* | *10* | *4013913* |
| 7/20/2003 | 2:01:14 | MICU | | heparin 25000 unit / 250 mL | 7450 unit/hr | 3000 | 2.48 | 10 | 1450 unit/hr | 5.14 | 4021746 |

FIG. 6

INTRAVENOUS MEDICATION HARM INDEX SYSTEM

BACKGROUND OF THE INVENTION

The present invention relates generally to systems and methods for managing patient care in a health care facility, and more particularly, to systems and methods for assessing the severity of averted medication errors.

Medication errors, that is, errors that occur in the ordering, dispensing, and administration of medications, regardless of whether those errors caused injury or not, are a significant consideration in the delivery of healthcare in the institutional setting. Additionally, adverse drug events ("ADE"), which are a subset of medication errors, defined as injuries involving a drug that require medical intervention, and representing some of the most serious medication errors, are responsible for a number of patient injuries and death. Healthcare facilities continually search for ways to reduce the occurrence of medication errors. Various systems and methods are being developed at present to reduce the frequency of occurrence and severity of preventable adverse drug events ("PADE") and other medication errors. In the administration of medication, focus is typically directed to the following five "rights" or factors: the right patient, the right drug, the right route, the right amount, and the right time. Systems and methods seeking to reduce ADE's and PADE's should take these five rights into consideration.

Delivery, verification, and control of medication in an institutional setting have traditionally been areas where errors can occur. In a typical facility, a physician enters an order for a medication for a particular patient. This order may be handled either as a simple prescription slip, or it may be entered into an automated system, such as a physician order entry ("POE") system. The prescription slip or the electronic prescription from the POE system is routed to the pharmacy, where the order is filled. Typically, pharmacies check the physician order against possible allergies of the patient and for possible drug interactions in the case where two or more drugs are prescribed, and also check for contra-indications. Depending on the facility, the medication may be identified and gathered within the pharmacy and placed into a transport carrier for transport to a nurse station. Once at the nurse station, the prescriptions are once again checked against the medications that have been identified for delivery to ensure that no errors have occurred.

Typically, medications are delivered to a nurse station in a drug cart or other carrier that allows a certain degree of security to prevent theft or other loss of medications. In one example, the drug cart or carrier is divided into a series of drawers or containers, each container holding the prescribed medication for a single patient. To access the medication, the nurse must enter the appropriate identification to unlock a drawer, door, or container. In other situations, inventories of commonly-used drugs may be placed in a secure cabinet located in an area at or close by a nurse station. This inventory may contain not only topical medications but oral, intramuscular ("IM")-, and intravenous ("IV")-delivered medications as well. Nurse identification and a medication order number are typically required to gain access to the cabinet.

The nurse station receives a listing of drugs to be delivered to patients at intervals throughout the day. A nurse or other care-giver or other qualified person reads the list of medications to be delivered, and gathers those medications from the inventory at the nurse station. Once all of the medications have been gathered for the patients in the unit for which the nurse station is responsible, one or more nurses then take the medications to the individual patients and administer the dosages.

Such a system may not be capable of thoroughly verifying that the appropriate medication regimen is being delivered to a patient in the case where IV drugs are being delivered. For example, a nurse may carry an IV bag to a particular patient area, hang the bag, program an infusion pump with treatment parameters, and begin infusion of the medication. However, even where the right medication arrives at the right patient for administration, incorrect administration of the medication may occur where the medication is to be administered using an automated or semi-automated administration device, such as an infusion pump, if the automated device is programmed with incorrect medication administration parameters. For example, even where the medication order includes the correct infusion parameters, those parameters may be incorrectly entered into an infusion pump, causing the infusion pump to administer the medication in a manner that may not result in the prescribed treatment.

One attempt at providing a system with built-in safeguards to prevent the incorrect entry of treatment parameters utilizes a customizable drug library which is capable of monitoring the parameter entry process and interacting with the care-giver should an incorrect entry or an out of range entry be attempted. In such a case, an alert is communicated to the care-giver that the parameter entered is either incorrect or out of a range established by the institution where care is being provided. Even though these customized drug libraries have provided a significant advance in the art for avoiding medication errors, they do not differentiate the alerts based on the severity of the medication error. It would be advantageous to provide an assessment of the severity or the "harm potential" of detected medication errors to enable the care-giver to respond more appropriately to each error.

Additionally, various methods have been used to record all of the activities surrounding the delivery of a treatment regimen, such as providing an infusion pump with a memory dedicated to storing a record of events related to a particular treatment. For example, in one system, an infusion pump has a memory in which treatment information, including treatment parameters, patient identification, care-giver identification and other information, is stored for later retrieval. Alternatively, the infusion pump may be programmed to store information related to only certain events occurring during treatment delivery, such as the occurrence of alarms or other alerts. Reports providing the details surrounding these alerts may be generated for review by the institution in order to assess current practices and identify ways to improve IV medication administration safety. However, these reports generally provide raw data that requires additional analysis before it is useful to an institution. Therefore, it would also be advantageous to provide an assessment of the severity or harm potential of each averted medication error to improve the institution's retrospective analysis of medication errors.

Hence what has been recognized as a need, and has heretofore been unavailable, is a system for managing patient care which includes assessment of the harm potential associated with averted IV medication errors to further improve delivery of health care to patients. The system would further be capable of providing appropriate alerts at the point of care on the basis of severity of the detected medication errors. The invention fulfills these needs and others.

INVENTION SUMMARY

Briefly, and in general terms, the present invention is directed to a system and method for assessing the severity of harm associated with averted IV medication errors and assigning a harm index value to medication errors to more efficiently monitor, track and correct these errors.

In one aspect of the present invention, there is provided a system for assessing the severity of medication errors associated with delivering medication to a patient comprising a first memory in which is stored a harm index database, the harm index database including harm index values associated with various medication errors, the harm index values representing the severity of the medication errors, a second memory in which is stored a log of medication errors, a processor operatively connected to the first and second memories and configured to determine an overall harm index value for each medication error in the log based on the harm index values stored in the harm index database associated with the medication errors, and means for reporting the overall harm index value for each medication error to a user.

In a more detailed aspect, the means for reporting the overall harm index value for each medication error to a user comprises a display operatively connected to the processor for displaying the overall harm index value for each medication error. In another detailed aspect, the means for reporting the overall harm index value for each medication error to a user comprises a printer operatively connected to the processor for printing a report of the overall harm index value for each medication error. In yet another detailed aspect, the system further comprises at least one patient care device for delivering medication to a patient for providing the log of medication errors and means for communicating the log of medication errors to the second memory.

In another detailed aspect, the harm index database further includes a plurality of harm index parameters relating to patient treatment, each harm index parameter being associated with harm index values representing the severity of medication errors associated with each harm index parameter, and wherein the processor is further configured determine the overall harm index value for each medication error in the log based on assessing the harm index values for each harm index parameter corresponding to each medication error. In further detailed aspects, the harm index parameters include drug type, dosage, level of care of the patient and detectability of the error. Each medication error in the log is defined by a plurality of treatment parameters and the processor is further configured to compare the harm index parameters to the treatment parameters for each medication error and assign a harm index value to each treatment parameter to determine the overall harm index value of each medication error.

In another aspect of the present invention, there is provided a system for assessing potential for harm of detected medication errors associated with delivering medication to a patient comprising a patient care device for delivering medication to a patient, means for entering values for medication administration parameters to program the patient care device to deliver medication to a patient, a memory associated with the patient care device in which is stored medication administration guidelines representing acceptable values for the medication administration parameters, a processor operatively connected to the memory and configured to compare the entered values to the acceptable values and indicate when an error representing a discrepancy between the values is detected, wherein the memory further stores a harm index database including harm index values representing potential for harm associated with a plurality of medication errors, and wherein the processor is further configured to determine an overall harm index value for the indicated error based on the harm index values associated with the corresponding medication error stored in the harm index database, and means for reporting the overall harm index value to a user.

In more detailed aspects, the means for reporting overall harm index value to a user comprises a display operatively connected to the processor for displaying the error and associated overall harm index value. The harm index database further includes a plurality of harm index parameters relating to patient treatment, each harm index parameter being associated with the harm index values according to the potential for harm of each harm index parameter, and wherein the processor is further configured to determine the overall harm index value for the indicated error based on the harm index values associated with the harm index parameters corresponding to the indicated medication error. In a further detailed aspect, the harm index parameters include drug type, dosage, level of care of the patient and detectability of the error.

In yet another aspect of the present invention, there is provided a patient care device for delivering medication to a patient comprising an input device for entering values for medication administration parameters for delivery of medication to a patient, a memory in which is stored medication administration guidelines representing acceptable values for the medication administration parameters and a harm index database including harm index values associated with a plurality of medication errors, the harm index values representing potential for harm of the medication errors, a processor operatively connected to the memory and configured to compare the entered values to the acceptable values and to determine an overall harm index value when the entered values do not match the acceptable values, the overall harm index value being determined based on the harm index values stored in the harm index database which are associated with the entered values, and means for reporting the overall harm index value to a user. In a more detailed aspect, the means for reporting the overall harm index value to a user comprises a display for displaying the overall harm index value to a user.

Also provided is a method for assessing the severity of medication errors associated with an administration of medication by a patient care device to a patient comprising detecting when a value of a treatment parameter entered into the patient care device is out of range by comparing the entered value to values stored in a library of acceptable values of treatment parameters, providing an alert that the entered value is out of range if the comparison indicated that the entered value is not found within the library of acceptable values, storing information concerning the alert in a memory of the patient care device, communicating the stored information in the memory of the medication administration device to a processor, analyzing the stored information by determining an overall harm index value for the alert represented by the stored information from a harm index database that assigns harm index values to various alerts, the harm index values representing the severity of the alert, and reporting the overall harm index value for the alert represented by the stored information to the care-giver.

In another method aspect of the present invention, there is provided a method for assessing the severity of medication errors associated with an administration of medication by a patient care device to a patient comprising detecting when a value of a treatment parameter entered into the patient care device is out of range by comparing the entered value to values stored in a library of acceptable values of treatment parameters, providing an alert that the entered value is out of range if the comparison indicated that the entered value is not found within the library of acceptable values, and determining a harm index value for the alert by comparing the entered treatment parameters values associated with the alert to a harm index database which provides harm index values representing the severity of an alert based on the treatment parameters associated with the alert.

Other aspects and advantages of the invention will become apparent from the following more detailed description when taken in conjunction with the accompanying drawings of illustrative embodiments.

BRIEF DESCRIPTION OF THE DRAWINGS

FIGS. 4A-4C show portions of a harm index database in accordance with aspects of the present invention;

FIG. 5 is a functional block diagram of the software modules that comprise the information and care management system of FIG. 1; and FIG. 6 presents a report of medication errors at a hospital including a harm index value for each error.

DETAILED DESCRIPTION OF THE PREFERRED EMBODIMENTS

The present invention provides a system and method for assessing a measure of harm for medication errors. Additionally, the system is capable of providing appropriate alerts at the point of care based on a calculated harm index value and/or retrospective reports detailing harm index values for various errors throughout the facility.

Figure 1:
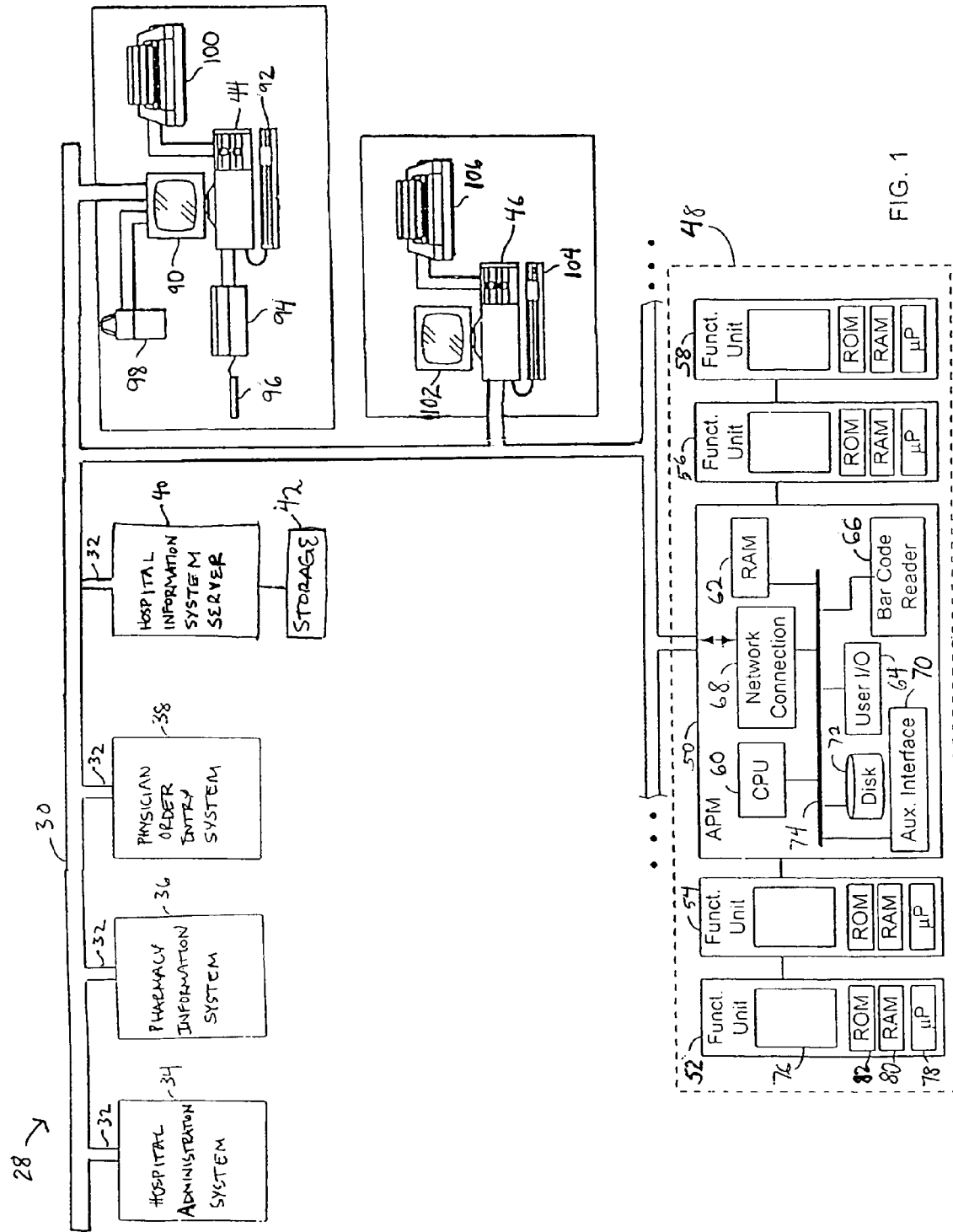
FIG. 1 is a schematic diagram of a hospital-wide information and care management system incorporating principles of the present invention.

Referring now to drawings in which like reference numerals are used to refer to like or corresponding elements among the figures, there is generally shown in FIG. 1 an integrated hospital-wide information and care management system 28 in accordance with aspects of the present invention. Various subsystems of the facility's information and care management system are connected together by way of a communication system 30. The communication system 30 may be, for example, a local area network ("LAN"), a wide area network ("WAN"), Inter- or intranet based, or some other telecommunications network designed to carry signals allowing communications between the various information systems in the facility. For example, as shown in FIG. 1, the communication system 30 connects, through various interfaces 32, a hospital administration system 34, a pharmacy information system 36, a physician order entry ("POE") system 38, and a hospital information system server 40 with associated storage 42. In one embodiment, the communication system also includes computer systems located in various departments throughout a hospital. For example, the communication system 30 of FIG. 1 optionally includes computer systems associated with a pharmacy central processing unit ("CPU") 44 and one or more nursing station CPUs 46. The network may also include computer systems for other departments such as a biomedical engineering department or a clinical laboratory. One or more patient care devices 48 may also be connected to the communication system 30.

The communication system 30 may comprise, for example, an Ethernet (IEEE 522.3), a token ring network, or other suitable network topology, utilizing either wire or optical telecommunication cabling. In an alternative embodiment, the communication system 30 may comprise a wireless system, utilizing transmitters and receivers positioned throughout the care-giving facility and/or attached to various subsystems, computers, patient care devices and other equipment used in the facility. In such a wireless system, the signals transmitted and received by the system could be radio frequency ("RF"), infrared ("IR"), or other means capable of carrying information in a wireless manner between devices having appropriate transmitters or receivers. It will be immediately understood by those skilled in the art that such a system may be identical to the system set forth in FIG. 1, with the exception that no wires are required to connect the various aspects of the system.

Each of the various systems 34, 36, 38 and 40 generally comprise a combination of hardware such as digital computers which may include one or more central processing units, high speed instruction and data storage, on-line mass storage of operating software and short term storage of data, off-line long-term storage of data, such as removable disk drive platters, CD ROMs, or magnetic tape, and a variety of communication ports for connecting to modems, local or wide area networks, such as the network 30, and printers for generating reports. Such systems may also include remote terminals including video displays and keyboards, touch screens, printers and interfaces to a variety of clinical devices. The processors or CPUs of the various systems are typically controlled by a computer program or programs for carrying out various aspects of the present invention, as will be discussed more fully below, and basic operational software, such as a Windows™ operating system, such as Windows NT™, or Windows 2000™, or Windows XP™, distributed by Microsoft, Inc., or another operating program distributed, for example, by Linux, Red Hat, or any other suitable operating system. The operational software will also include various auxiliary programs enabling communications with other hardware or networks, data input and output and report generation and printing, among other functions.

Patient care device 48 may comprise any of a variety of clinical devices such as an infusion pump, physiological monitor (e.g., heart rate, blood pressure, ECG, EEG, pulse oximeter, capnography unit, and other patient monitor), a therapy device, and other drug delivery device. In one embodiment, patient care device 48 comprises a modular system similar to that described in U.S. Pat. No. 5,713,856 to Eggers et al., which is incorporated herein by reference. In this embodiment, the patient care device 48 comprises an advanced programming module 50, also referred to as interface unit 50, connected to one or more functional modules 52, 54, 56, 58. Interface unit 50 includes a central processing unit 60 connected to a memory, e.g. random access memory ("RAM") 62, and one or more interface devices such as user interface device 64, a coded data input device 66, a network connection 68, and an auxiliary interface 70 for communicating with additional modules or devices. Interface unit 50 also preferably, although not necessarily, includes a main non-volatile storage unit 72, preferably a hard disk drive, for storing software and data and one or more internal buses 74 for interconnecting the aforementioned elements. Alternatively, patient care device 48 or other patient care devices connected to the network may represent single-module patient care devices that include the same components as the interface unit 50.

In a typical embodiment, user interface device 64 is a touch screen for displaying information to a user and allowing a user to input information by touching defined areas of the screen. Alternatively, user interface device 64 could include any means for displaying and inputting information, such as a monitor, a printer, a keyboard, softkeys, a mouse, a track ball and/or a light pen. Coded data input device 66 is preferably a bar code reader capable of scanning and interpreting data printed in bar coded format. Alternatively, data input device 66 could be any device for entering coded data into a computer, such as devices for reading magnetic strips, PCMCIA smart cards, radio frequency cards, memory sticks, CDs, DVDs, or any other analog or digital storage media. Other examples of data input device 66 include a voice activation or recognition device or a portable personal data assistant ("PDA"). Depending upon the types of interface devices used, user interface device 64 and coded data input device 66 may be the same device. Alternatively, although data input device 66 is shown in FIG. 1 to be disposed within interface unit 50, one skilled in the art will recognize that data input device 66 may be integral within pharmacy information system 36 or located externally and communicating with pharmacy information system 36 through an RS-232 serial interface or any other appropriate communication means. Auxiliary interface 70 is preferably an RS-232 communications interface, however any other means for communicating with a peripheral device such as a printer, patient monitor, infusion pump or other medical device may be used without departing from the scope of the invention.

Network connection 68 is preferably a direct network connection such as a T1 connection, an integrated services digital network ("ISDN") connection, a digital subscriber line ("DSL") modem or a cable modem. Alternatively, any direct or indirect network connection may be used, including, but not limited to a telephone modem, an MIB system, an RS232 interface, an auxiliary interface, an optical link, an infrared link, a radio frequency link, a microwave link or a WLANS connection.

Functional modules 52, 54, 56, 58 are any devices for providing care to a patient or for monitoring patient condition. In one embodiment of the present invention, at least one of functional modules 52, 54, 56, 58 is an infusion pump module such as an intravenous infusion pump for delivering medication or other fluid to a patient. For the purposes of this discussion, functional module 52 is an infusion pump module. Each of functional modules 54, 56, 58 may be any patient treatment or monitoring device including, but not limited to, an infusion pump, a syringe pump, a PCA pump, an epidural pump, an enteral pump, a blood pressure monitor, a pulse oximeter, a capnography unit, an EKG monitor, an EEG monitor, a heart rate monitor or an intracranial pressure monitor. Alternatively, functional module 54, 56 and/or 58 may be a printer, scanner or any other peripheral input/output device.

Each functional module 52, 54, 56, 58 communicates directly or indirectly with interface unit 50, with interface unit 50 providing overall monitoring and control of device 48. In a preferred embodiment, functional modules 52, 54, 56, 58 are connected physically and electronically in serial fashion to one or both ends of interface unit 50 as shown in FIG. 1 and as detailed in Eggers et al. However, one skilled in the art will recognize that there are other means for connecting functional modules with the interface unit which may be utilized without departing from the scope of the invention. It will also be appreciated that devices such as pumps or monitors that provide sufficient programmability and connectivity may communicate directly with the network without a separate interface unit. As described above, additional medical devices or peripheral devices may be connected to patient care device 48 through one or more auxiliary interfaces 70.

Each functional module 52, 54, 56, 58 typically includes module-specific components 76, a microprocessor 78, a volatile memory 80 and a nonvolatile memory 82 for storing information. It should be noted that while four functional modules are shown in FIG. 1, any number of devices may be connected directly or indirectly to central computer 50. The number and type of functional modules described herein are intended to be illustrative, and in no way limit the scope of the present invention. Module-specific components 76 include any components necessary for operation of a particular module, such as a pumping mechanism for infusion pump module 52.

While each functional module is typically capable of a least some level of independent operation, interface unit 50 monitors and controls overall operation of device 48. For example, as will be described in more detail below, interface unit 50 provides programming instructions to the functional modules 52, 54, 56, 58 and monitors the status of each module.

As shown in FIG. 1, the computer system associated with the pharmacy at the healthcare facility comprises the central processing unit 44 to which is attached a video display 90 and a keyboard 92 for entry and display of patient information and drug parameters. Also attached to the pharmacy CPU is a bar code reader 94 with a light emitting and receiving wand 96 which is adapted to read barcode labels that may be attached to drug containers, equipment, or caregiver identification badges. Also connected to the pharmacy CPU 44 is a bar code printer 98 and a printer 100 used for generating reports containing information about patient history and/or patient treatment. The printer 100 may also be used to print barcode labels generated by the pharmacy CPU 44 after patient or drug data is input by a technician or pharmacist into the pharmacy computer 44 using the keyboard 92 or other means.

Another computer, herein referred to as the nursing CPU 46, is located at a nursing station. Nursing stations are typically located in various sections and/or floors of a hospital or clinic and typically provide a central location for record storage and monitoring for a number of patient beds. The nursing CPU 46 located at the nurse station typically includes a video display 102 for displaying patient or other information pertaining to the operation of the particular unit of the institution, and a keyboard 104, mouse, touch screen, or other means for entering patient data or specific commands instructing the nursing CPU 46 to generate reports relating to either the patient's medical history or the course and progress of treatment for an individual patient on the attached printer 106 or on the video display 102. As will be discussed more fully below, the nursing station CPU 46 may also generate other reports such as, for example, a printout of drugs scheduled to be administered to patients, productivity measurements such as, for example, the amount of time a nurse spends with a patient or other reports useful for assisting in the efficient operation of the particular unit or the hospital. For example, a report listing the actual times of administration versus the scheduled times for administration may be prepared to assist in evaluation of staffing requirements.

Each care unit associated with the nursing station typically comprises one or more patient beds located in private rooms, shared rooms, or open or semi-open wards that contain multiple beds. In accordance with an embodiment of the present invention, each private room, semi-private room, or ward area has at least one bedside CPU (not shown) for monitoring and treating one or more patients. The bedside CPU may be a system having a computer or processor located in the general vicinity of a patient. Such a computer or processor, besides being embodied in a bedside computer, may also be incorporated in a handheld or vital signs device, a laptop computer, a PDA and the like. In one embodiment, the interface unit acts as a bedside CPU that is associated with a single patient.

According to one embodiment of the present invention, patient care device 48 includes a medication harm index system for analyzing detected medication errors, and more specifically, for assessing the potential for harm associated with the errors. A harm index database, as will be discussed in more detail with respect to FIGS. 4A-4C, may be accessible to the patient care device to provide harm index values for various medication administration parameters for calculating an overall harm index of a medication error. The term "database" or "data base" as used herein will be understood by those skilled in the art to be used as is commonly understood, that is, the term "data base" refers to a collection of values or information organized, formatted, and stored in such a manner as to be capable of being retrieved and analyzed using an appropriate program contained in software or other form. The overall harm index represents a score or rating indicative of the risk or potential for harm associated with the error and can be used to alert a caregiver as to the severity of a detected medical error so appropriate action may be taken at the point of care.

Such a system may be used with various patient care devices, but is particularly useful for IV infusion pumps that require programming, such as pump 52. Single module infusion pumps that do not include an interface unit may also incorporate the medication harm index system of the present invention. Harm indexing of errors may be used in conjunction with any system at the healthcare facility for detecting errors in medical treatments. For example, some infusion pumps compare entered infusion parameters against a record of the prescribed parameters accessible from the network, such as from the pharmacy information system 36, to ensure accuracy. In the case where the parameters do not match, the care-giver could be informed of the severity of the error by providing a harm index value. As will be discussed in more detail below, the system is especially useful in conjunction with medication administration guidelines, such as a drug library, used for detecting incorrect parameters programmed into infusion pumps.

Figure 2:
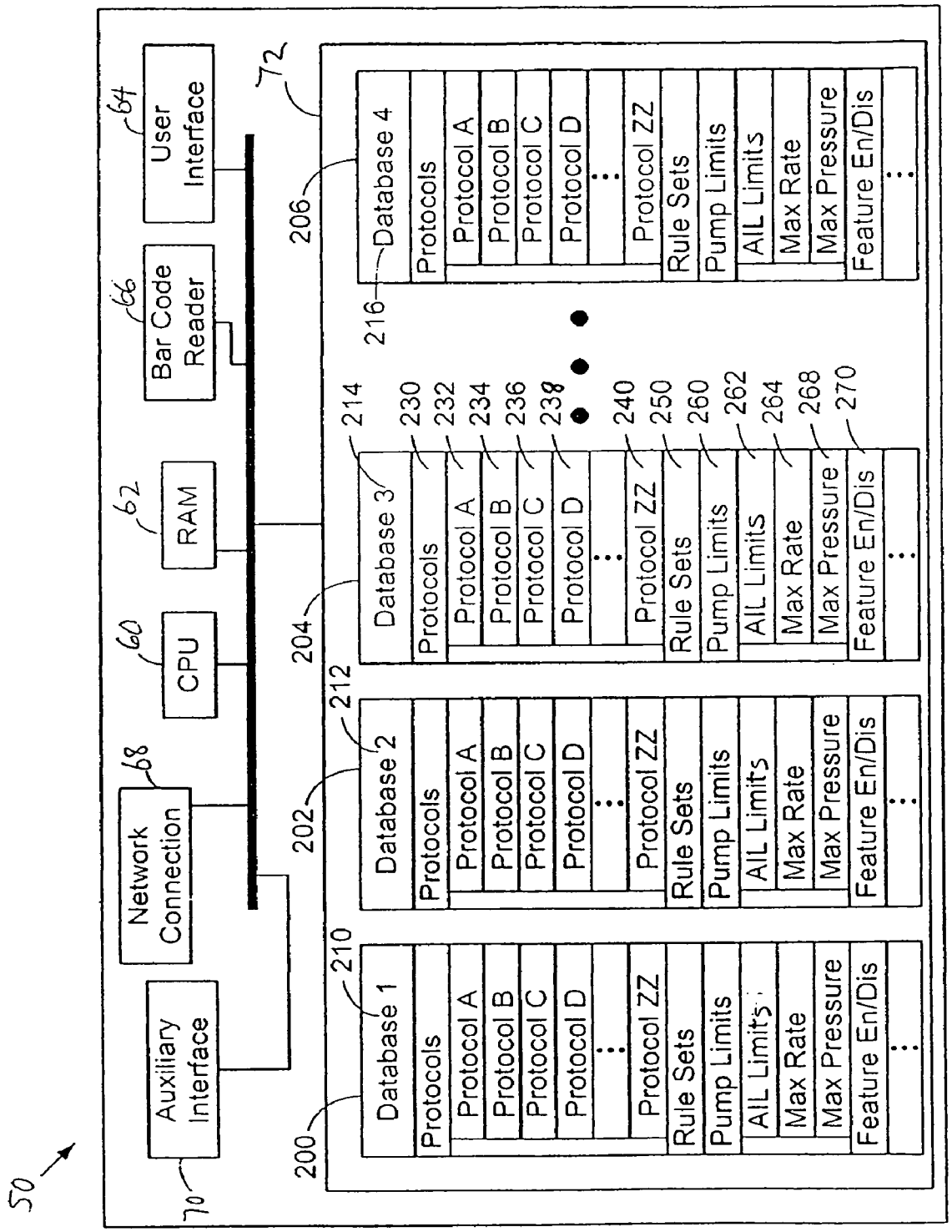
FIG. 2 is a schematic diagram of an interface unit and the contents of its memory according to aspects of the present invention.

Patient care device 48 is capable of storing one or more electronic databases, such as databases 200, 202, 204 and 206 shown in FIG. 2, containing institutionally-established guidelines for medical treatments. These institutional guidelines may provide appropriate parameters for administration of various medications. For example, the guidelines may include institutionally established guidelines or limits on drug administration parameters, such as dosage, frequency of administration, and other delivery related information such as, for example, appropriate flow rates and infusion durations for programming infusion pumps.

In one embodiment of the present invention, the patient care device 48 is also capable of operating in several different modes, or personalities, with each personality defined by a configuration database. A particular configuration database stored in a patient care device is selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's location in the hospital or hospital computer network. Patient care information may be entered through interface device 64, 66, 68 or 70, and may originate from anywhere in network 30, e.g. from the hospital administration system 34, pharmacy information system 36, or any other system or department in the facility.

Data to and from the various data sources can be converted into network-compatible data with existing technology, and movement of the information between the medical device and network can be accomplished by a variety of means. For example, patient care device 48 and the network may communicate via automated interaction and/or manual interaction. Automated interaction may be continuous or intermittent and may occur through direct network connection 68 (as shown in FIG. 1), or alternatively through RS232 links, MIB systems, RF links such as BLUETOOTH (Amtel Corp., San Jose, Calif.), IR links, WLANS, digital cable systems, telephone modems or other communication means. Manual interaction between patient care device 48 and the network involves physically transferring, intermittently or periodically, data between systems using, for example, user interface device 64, coded data input device 66, bar codes, computer disks, PDAs, memory cards, or any other media for storing data. Preferably, the communication means is bidirectional with access to data from as many points of the distributed data sources as possible. Decision-making can occur at a variety of places within the network. For example, and not by way of limitation, decisions can be made in hospital administration system 34, pharmacy information system 36, other departments or systems such as a nursing station or a pharmacy CPU, or within patient care device 48 itself.

Referring to FIG. 2, in one embodiment of the present invention, interface unit 50 of patient care device 48 includes a plurality of configuration databases 200, 202, 204 and 206. Although this embodiment is primarily described with respect to the interface unit 50 of patient care device 48, it will be understood that the configuration databases may similarly be loaded into the other patient care devices such as infusion pumps that are not part of a modular system. The configuration databases are preferably stored in memory 72 of interface unit 50, however one or more databases may be stored within a functional module 52, 54, 56, 58 (FIG. 1). One skilled in the art will understand that, while memory 72 is preferably an internal hard disk, any permanent or removable storage media including, but not limited to, CD-ROM, EEPROM, diskette, tape, external hard disk, memory card, flash memory, etc. may be used. Optionally, portions of configuration databases 200, 202, 204, 206 may be stored in volatile memory such as RAM 62.

Figure 3:
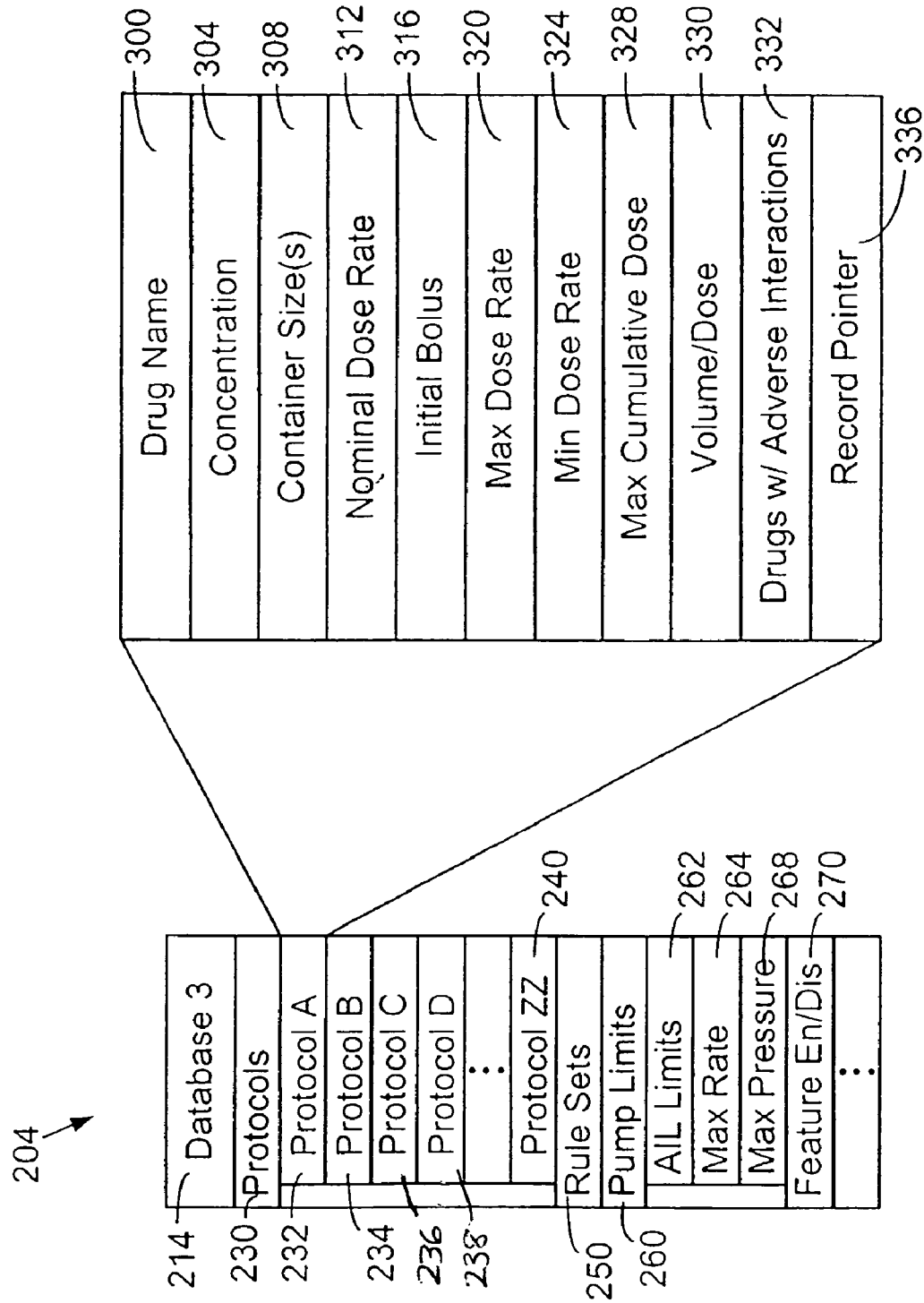
FIG. 3 is a schematic diagram illustrating a configuration database according aspects of the present invention.

With reference to both FIGS. 2 and 3, each configuration database 200, 202, 204, 206 preferably includes a unique database identifier, or pointer, 210, 212, 214, 216, for identifying the respective database. Each database 200, 202, 204, 206 includes a plurality of fields which define, for example, available treatment protocols, drug library information, rule sets, device features, and possibly other information for defining particular operating parameters for patient care devices. Each configuration database 200, 202, 204, 206 defines a specific operating environment, or personality, for the patient care device 48. The individual configuration databases may be treatment location specific (e.g. intensive care unit [ICU], neonatal intensive care unit [NICU], pediatrics, oncology, etc.), disease state specific (intracranial pressure management, bone marrow transplant, etc.), user specific (LPN, RN, physician, etc.), or created by any other rationale. For example, according to one embodiment of the present invention, when patient care device 48 is located in the ICU it utilizes configuration database 200, and when device 48 is located in the NICU it utilizes configuration database 202. Each database 200 and 202, respectively, contains particular operating parameters, treatment protocols, features, etc. that configure device 48 for use with patients in that unit of the hospital.

It should be noted that while FIGS. 2 and 3 show that each database includes the same categories and types of information, the databases may vary considerably in terms of the types and amounts of information they contain. Each of the various configuration databases, when selected, at least in part defines the operating environment of device 48 and includes a number of protocols or groups of default operating parameters.

FIG. 3 is a more detailed representation of a sample configuration database 204 according to one embodiment of the present invention. Configuration database 204 includes a protocol module 230 comprising a plurality of protocols 232, 234, 236, 238, 240. Each protocol includes a plurality of fields of default operating parameters. In some cases an infusion protocol may include a complete detailed infusion instruction with all of the default parameter values defined. Other infusion protocols may have partially defined parameters with additional data entry required by the user at the point of care. For example, protocol A 232 of FIG. 3 includes fields of default operating parameter values and other data for controlling a medication infusion pump. The fields of this example include drug name 300, concentration 304, container size(s) 308, nominal dose rate 312, initial bolus 316, maximum dose rate 320, minimum dose rate 324, maximum cumulative dose 328, drug incompatibility 332 and an ID field, record pointer 336, for identifying or "calling" the protocol record. Each field typically includes stored default parameter values that collectively define a specific infusion protocol. Some fields, such as drug incompatibility 332, include a reference or link to another database or drug library containing relevant information. Such references to commonly used data libraries allow data to be shared between protocols and/or configuration databases to avoid duplicate storage and entry and to allow efficient updating of database information. Similarly, all protocols need not be stored within each configuration database. Rather, protocols from different configuration databases may be saved in a master database or library, with each individual configuration database containing reference links to particular protocols stored in the library. Such an arrangement is advantageous because it avoids duplicate storage of identical protocols and facilitates updating of library information.

When such a protocol is selected certain information must be provided. For example, device 48 may query the network to automatically obtain data such as patient weight from the patient's electronic records in hospital administration system 34, critical dosage parameters from pharmacy information system 36 and double check with a laboratory for recent test results which may contraindicate the prescribed medication. A double check with pharmacy information system 36 of information coded on the drug prescription label also may be automatically performed. Alternatively, the user may enter data such as the patient weight and total dosage directly into the device. In one embodiment of the invention, information in a drug specific protocol is a superset of the information in the "drug library". Consequently, if the user selects a drug name, then certain parameters in the record are applied. Such parameters would typically include the drug name, delivery rate limits, units of delivery, possibly concentration and container size. The user would enter or scan in missing data such as patient weight, drug amount, diluent volume, dosage rate, total dosage and confirm the automatically selected parameters as prompted.

Different protocols typically include different fields and/or different parameter values. Thus, Protocol B 234 might include additional fields compared to Protocol A 232, where the additional fields define instructions and/or parameters for implementing one or more different infusion types such as primary/secondary infusion, multichannel coordinated infusion and multidose protocols. Alternatively, Protocol B 234 could include the same fields as Protocol A 232, and differ only in terms of one or more parameter values in one of the fields. For example, both protocols could be for infusion of the drug dopamine, where one protocol has a concentration 304 value of 400 mg/250 mL while the other has a concentration 304 value of 800 mg/250 mL.

Referring again to FIGS. 2 and 3, the Rule Sets module 250 of database 204 includes rules and/or algorithms that may be used to help define particular parameters within a database. For example, Rule Sets module 250 could include an algorithm that modifies the maximum allowable infusion rate or some other parameter based upon data obtained from other sources in network 30, such as patient age, body weight or medical history from hospital administration system 34 or test results from the laboratory. Other rule sets in the Rule Sets module 250 may provide warnings or recommendations upon the occurrence of particular events within pump module 52, such as occlusion of the infusion line.

Still other rule sets within module 250 may contain algorithms that utilize measurements from one or more functional modules to modify operation of another functional module. For example, module 250 may contain a rule set that monitors blood pressure and intracranial pressure in a head trauma patient and calculates resulting perfusion pressure. The system then notifies the user when perfusion pressure falls outside of a defined range and recommends adjusting infusion rate of a therapeutic agent to increase blood pressure or to decrease intracranial pressure.

As shown in FIGS. 2 and 3, the Pump Limits module 260 of database 204 contains information that defines the overall operating limits of infusion pump module 52 and other pump devices, if any, attached to interface unit 50. The Pump Limits module 260 typically includes at least three fields, Air In Line (AIL) Limits 262, Max Rate 264, and Max Pressure 268. Because the Pump Limits module 260 of each configuration database 200, 202, 204, 206 potentially contains different parameters and values, module 260 helps define the operating characteristics or mode in which device 50 operates when a particular configuration database 200, 202, 204, 206 is active.

AIL Limits 262 defines an allowable limit for the amount of air in an infusion line connected to a patient. Allowable AIL Limits may differ for particular patients or particular locations in the hospital. For example, an allowable limit of 50 μL may be set for pediatric patients, while a limit of 100-200 μL is used for general adult patients and 500 μL for operating room and/or trauma patients.

Max Rate 264 defines the maximum allowable infusion rate for an infusion pump operating under that particular configuration database 204. Again, the defined Max Rate 264 values may differ among patient class, attributes, location, etc. For example, the maximum rate for delivering heparin to pediatric patients may be set at 10 units/Kg/hr, while adult patients have a limit of 500-2000 units/hr.

Feature Enable/Disable module 270 of configuration database 204 defines which particular features, such as infusion types for pumps, are available to the user of patient care device 48 when configuration database 204 is activated. In a preferred embodiment of the present invention, patient care device 48 is capable of supporting a wide variety of such features, ranging from simple primary infusions used for hydration and keep-vein-open ("KVO") applications to complex multichannel delivery applications.

Referring now to FIGS. 4A-4C, according to one embodiment of the present invention, the contents of a harm index database 400 may be stored in memory 72 of the interface unit 50. Alternatively, the database 400 may be stored in the memory 82 of functional module 52 or in a remote computer that may be accessed by the patient care device 48 via the network 30. The harm index database 400 includes harm index values for various harm index parameters or factors related to medication administration. In FIGS. 4A-4C, the harm index parameters are shown organized into various sub-databases within database 400. The parameters include the drug type 402 and dosage 404 (FIG. 4A), the patient's level of care 406 (FIG. 4B), and detectability of the error 408 (FIG. 4C).

The drug type parameter 402 defines the inherent risks of particular drugs. Each drug is assigned a value according to its risk or potential for causing harm to a patient when incorrectly prescribed to be used in the calculation of the overall harm index for a medication error. For example, in the embodiment shown in FIG. 4A, drugs are categorized as high risk 410, medium risk 412 or low risk 414. Heparin, for instance, would generally be classified as a high risk drug, while dopamine would be classified as a medium risk drug. Each risk category 410, 412 or 414 is assigned a harm index value representing a score or rating according to its risk. As shown in FIG. 4A, the value also depends on the magnitude of the dose, as will be discussed in more detail below. The data shown in FIG. 4A may be associated with a separate drug library that includes a list of drugs and reference links for each drug to the appropriate harm index fields in the harm index database 400.

The dosage parameter 404 defines the risk associated with the dosage of the medication and provides harm index values for various dosage amounts in accordance with their risk. For example, dosage amounts may be categorized as low risk 416, moderate risk 418 or high risk 420, with each category being associated with a harm index value. Each dose risk category may also be associated with a range of harm index values that are dependent on the drug type parameter 402. For example, in FIG. 4A, the combined harm index value for a low risk drug-low risk dose is 1.5, for a low risk drug-moderate risk dose is 2 and for a low risk drug-high risk dose is 3. The combined harm index value for a medium risk drug-low risk dose is 2, for a medium risk drug-moderate risk dose is 4 and for a medium risk drug-high risk dose is 6. The combined harm index value for a high risk drug-low risk dose is 3, for a high risk drug-moderate risk dose is 6 and for a high risk drug-high risk dose is 9.

The risk categories for the dosage parameter 404 may be determined based on the magnitude of the dosing error, such as the ratio of the erroneous dosage to the maximum dosage limit. The maximum dosage limit may correspond with the maximum dose rate 320 (FIG. 3) for the selected configuration database. For example, in FIG. 4A, a low risk dose associated with a low risk drug is 1 to 4 times the maximum dosage limit while a high risk dose associated with a low risk drug is greater than 10 times the maximum dosage limit. Further, a low risk dose associated with a high risk drug is 1 to 1.5 times the maximum dosage limit while a high risk dose associated with a high risk drug is greater than 2.5 times the maximum dosage limit. While this ratio is expected to be provide an accurate assessment of the risk associated with the overdose, the magnitude of the error may alternatively be weighed against the actual prescribed dose or the average dose. The harm index database 400 may also include harm index values for doses that are below either the minimum dose rate, the prescribed rate, or the average rate.

The level of care parameter 406 defines the risk for various patient care levels at a healthcare facility. As shown in FIG. 4B, different harm index values are provided for levels of care, including General 422, Intermediate 424, Adult ICU 426 and PICU/NICU 428. The General level of care 422 is low risk with a harm index value of 1, while Intermediate 424 has a harm index value of 1.2, Adult ICU 426 has a harm index value of 2 and PICU/NICU 428 is high risk with a harm index value of 3. The level of care may be determined by the particular configuration database 200, 202, 204 or 206 (FIG. 2) selected. Additional levels of care may also be included, such as those described with respect to the configuration databases (e.g., pediatrics and oncology). The level of care may alternatively be determined by other measures, such as Apache scores or other widely-used systems for scoring the criticality of a patient's clinical status.

The detectability parameter 408 defines the likelihood that the error would have been detected by a care-giver before a harmful adverse drug event occurs and provides harm index values based on the amount of monitoring provided to a patient. FIG. 4C shows that a "likely" detectability 410 is assigned a harm index value of 1 and an "unlikley" detectability 412 receives a harm index value of 2. As an example, an overdose of dopamine to an ICU patient would typically be detected quickly because the patient would be under constant monitoring of vital signs and any adverse effects would be detected immediately. However, in a case where heparin is prescribed to a patient, detection of an overdose of heparin would typically be unlikely until after a major adverse drug effect occurs.

The CPU 60 of the interface unit 50 is configured to determine the harm index values for the individual parameters 402, 404, 406 and 408 for various errors that have been detected through use of the medication administration guidelines or other verification procedure used by the patient care device 48. Alternatively, the processor 78 of the infusion pump module 52 may perform the analysis to determine the harm index values. The harm index values for each parameter may then be combined, for example by adding, to yield an overall harm index value. For example, the overall harm index value for an error according to the FIG. 4A-4C ratings would range from 3.5 to 14, with the low end of the range indicating a minimal harm potential (i.e., no or minor clinical effect), the middle of the range indicating a moderate harm potential (i.e., a probable significant clinical effect), and the high end of the range indicating a severe harm potential (i.e., a potentially-life threatening clinical effect).

Alerts may be generated to notify the nurse of the error and may be tailored based on the severity of the error as indicated by the overall harm index value. The harm assessment system may permit several alerting levels to indicate the criticality of the error by varying the loudness or pattern of an audible alarm or by varying the display of a visual alarm. The criticality of the error may also determine whether the alert is provided at the point of care or also at a remote location such as a nurse's station or whether the alert causes the nurse or clinician to be paged. In one embodiment of the present invention, the harm index values may be used to determine whether a "hard" or "soft" limit value should be subsequently applied to a parameter in the medication administration guidelines. A soft limit, for example, may be assigned for drugs with low harm index values and would permit a caregiver to override the alert, while a hard limit would prevent an override.

Although four harm index parameters 402, 404, 406 and 408 have been described herein, it will be understood to one skilled in the art that other factors may be included in the harm assessment. Additionally, other means may be used to define and score a particular parameter. For example, patient-specific information such as laboratory results or age may be included either as a separate factor or integrated into the level of care parameter 406. The factors and harm index values in the database 400 may be initially developed through consultation with healthcare facilities and then be provided in the database 400 as predefined fields to provide a uniform harm index rating system. While this approach serves to promote standardization of medication error assessment in the healthcare industry, an editing tool (not shown) may alternatively be provided to allow customization of a harm index database 400 by individual facilities.

Although depicted in FIG. 1 as being connected directly to a hospital network, it is not necessary for patient care device 48 to be connected to a network. The user interface device 64 of the interface unit 50, for example, may be used to provide any information that would otherwise be obtained through the network from a remote system. In another embodiment, the patient care device 48 may be indirectly connected to the network, such as through a PDA or other bedside CPU.

In another embodiment, the harm index system may also be used to provide retrospective analysis of averted medication errors, providing an overall harm index value to each averted error for analysis purposes. In this embodiment, a database of alert or "event" logs may be stored in a memory of a hospital computer. The logs may be stored directly in the memory 72 or 82 of the patient care device 48 and may also be stored in memory 42 associated with the hospital information system server 40. The hospital information system server 40 generally stores programs and data input and collected by the various computers in the network. Various application modules of the information and care management system 28, including a harm index assessment module, may be resident in each of the computers in the network and will be discussed in more detail below. Analysis of the alert logs may be performed by the pharmacy CPU 44, the nursing CPU 46 or a processor at another work station in the facility such as a biomedical work station. Alternatively, the processing may be performed at the hospital information system server 40 with the module being accessed at a work station.

Referring now to FIG. 5, a block diagram illustrating the various application software modules comprising an illustrative embodiment of the care management system of the present invention is shown. The care management system's application software is modular in construction to allow installation and operation of the system with only one or more of the application software groups present. This provides flexibility in meeting the widely varying needs of individual institutions where cost and complexity may be an issue or where the full system is not needed. Each of the modular applications, however, is fully integratible into the system.

The programs of the information and care management system 28 control alarms or alerts generated by one of the modular applications. Alarms are routed automatically to the appropriate video display. For example, an occlusion alarm generated by a pump 52 may remain local for a predetermined period. After that period the interface unit 50, or the patient's bedside computer, may then broadcast the alarm by causing the alarm to be communicated over the communication system 30 to alert other hospital staff of a potential problem or to cause a particular person responsible for the care of a patient, such as, for example, a physician or nurse, to be paged.

Each of the modular applications will now be described in detail. The operation of each of these modular applications in a clinical setting will be discussed more fully below. The medical administration management module 500 integrates medical order information, infusion pump monitoring, and barcode technology to support the real-time verification and charting of medications being administered to a patient. The medical administration management module 500 creates and maintains an on-line, real-time, patient-specific medication administration record ("MAR") or integrated medication administration record ("IMAR") for each patient. This medical administration management module 500 contains all of the information generated in the institution regarding the care provided to the patient. The medical administration management module 500 gathers information from the various nursing CPUs 46 (FIG. 1) and various patient care devices 48 or bedside CPU's comprising the peripheral hardware of the information and care management system 28 that is distributed throughout the institution. For example, when a physician attending a patient diagnoses an illness and determines an appropriate course of treatment for the patient, the physician may prepare a handwritten medical order specifying the desired therapeutic treatment as well as any appropriate parameters such as dosage and/or period of administration. The written prescription is sent through the institutional mail system to the pharmacy where it is then entered into the pharmacy information system 36 through a dedicated terminal, or other means, and into the care management system 28.

In another embodiment, the physician may enter the order directly into the POE system 38 which transmits the order to the pharmacy information system 36. The physician may also access the pharmacy information system 36 through another dedicated terminal such as a nursing CPU 46. Alternatively, the treatment order may be entered by a nurse or other qualified caregiver into either the pharmacy information system 36 or the nursing CPU 46.

Typically, a patient identification bracelet is used in hospitals and other institutional settings to ensure that each patient is able to be identified even if the patient is unconscious or otherwise unable to respond to questioning. A barcode is printed on a label that is attached to the patient identification bracelet and has encoded within its sequence of bars the information necessary to identify the patient. This barcode may be read using a computerized barcode reader, such as those shown connected to the pharmacy CPU 44 and patient care device 48 (FIG. 1). Drug containers may also be identified by a bar code label that represents the patient identification and the medical order number, and any other information the institution finds helpful in dispensing the drug and tracking the treatment. The barcode may also be read using a barcode reader, and, using suitable application software such as that included within the medical administration management module 500, discussed below, can be used to link the drug container and its contents with the patient identification bracelet affixed to a patient to ensure the right drug is delivered to the right patient at the right time in the right manner. Such identification bracelets and labels may alternatively include a passive device, such as RF identification, magnetic stripes, smart chips and other wireless devices that are capable of being interrogated and communicating information to a querying device, instead of a barcode.

When the medication to be administered is of the type that is typically delivered to the patient using an infusion pump, the medical administration management module 500 automatically records the start time of the infusion, queries the pump periodically throughout the infusion and maintains a continuous log of the infusion, and records the end time of the infusion and the volume infused in a patient's MAR.

Because the medical administration management module 500 maintains an on-line, real-time, patient specific graphical medication administration record that includes both past, present and future scheduled medications, a nurse may select a scheduled dosage on the MAR and indicate that it will not be administered for specified reasons selected from a list of options that are dependent upon the health status of the patient at a particular time. This system also allows a nurse to select a scheduled dose on the MAR, and record notes and observations about the dose selected from a list of options. The medical administration management module 500 also provides on-line, real-time help screens that can be accessed by a nurse or other caregiver to display specific information about selected medication and dose to be dispensed.

The medical administration management module 500 provides a list of on-going infusions that can be displayed on the video display of the pharmacy CPU 44. Drug administrations that will terminate within a preselected time period may be distinguished from other administrations by color highlighting or other means. The time remaining, drug, and patient name are presented as well as buttons for program control.

The medical administration management module 500 records and maintains in a stored file a log of alerts that are generated when any discrepancy is identified, for example, during the verification process which will be discussed more fully below. The medical administration management module 500 also allows the nurse to acknowledge and correct the discrepancy in real-time, or override the alert by entering the appropriate command. Even where the nurse is allowed to override the alert, the medical administration management module 500 prompts the nurse for a reason for each alert override and then automatically enters the reason into the MAR for the patient.

The medical administration management module 500 assists the nurse or other health care professional in efficiently delivering care to the patients by providing the ability to perform on-line queries of the patient's MARs and produce reports designed to assist the nurse in planning medication administration and in scheduling the workload of dispensing the medication to the many patients for which a nursing unit is typically responsible. For example, the video display may be color coded to indicate the status and schedule of each drug administration. A drug delivery window extending from thirty minutes prior and thirty minutes after the scheduled administration time may be indicated by a yellow band on the display. Other reports such as a task list may, for example, include scheduling of drug administrations to ensure proper medication of the patient while distributing the workload over a period of time to ensure that all medication is given promptly. The system may also display either visuals alerts on the nurse station video display 102 or produce a printed report on the printer 106 to provide a permanent record of any medication administration that is running late or has been rescheduled. The medical administration management module 500 may be programmed to operate in an automatic fashion, automatically providing standard reports at the nursing station at predetermined intervals, such as, for example, every 30 minutes, as determined by the needs of the particular nursing unit and institution.

The clinical monitoring and event history module 502 shown in FIG. 5 is designed to monitor a variety of clinical devices, including patient care device 48, attached to the network in a real-time manner and provides information about those devices to monitoring stations located elsewhere on the network. For example, the clinical monitoring and event history module 502 can be configured to monitor a plurality of clinical devices that are in use to deliver medication to patients in the private rooms, semi-private rooms or ward areas in a nursing unit. The clinical monitoring and event history module 502 retrieves real-time data from each device, and displays a visual representation of each device including all significant data related to its status and settings on the video display 102 connected to the Nursing CPU 46 (FIG. 1). For example, in the case where the clinical monitoring and event history module 502 is monitoring infusion pump 52, a nurse at the nursing station can access the status for that pump wherein the display 102 attached to the nurse CPU 46 then displays information regarding the status of the infusion being performed at that time. For example, information can include the name of the drug being infused, the patient's name, the scheduled start, the actual start of infusion, the scheduled end of infusion, the projected end of infusion, the amount of drug infused, the amount of drug remaining to be infused and any alert or discrepancy conditions that may need attention by the nurse. Because the information and care management system 28 is a fully integrated system, the medical administration management module 500 works in concert with the clinical monitoring and event history module 502 so that a nurse, doctor or technician, after evaluating the status of the infusion displayed on the video display at the nursing CPU 46, a bedside CPU or other remote (i.e., not at the location of the patient) computer system, including a laptop or PDA, may adjust the infusion regimen accordingly using, for example, the keyboard or touch screen of the computer.

The clinical monitoring and event history module 502 may also be programmed to immediately display alarm conditions on remote monitoring screens, such as the video display 102 attached to the nursing CPU 46, as the alarm occurs. For example, the status of each patient's infusion can be represented on a video display at the nursing station. When an alert occurs, the box representing the patient's room flashes red to attract attention to the alert. Displaying the alarm condition in this manner allows a nurse to quickly and easily identify the patient from the nursing station and take appropriate action to address the condition causing the alarm. The system may also be programmed to display certain alarms that have been identified as particularly important events at other video displays located throughout the institution, such as the video display 90 attached to the pharmacy CPU 44 located in the institution's pharmacy.

In one embodiment of the invention, a harm index assessment module 504 shown in FIG. 5 analyzes alert logs collected from one or more patient care devices 48 to determine harm index values associated with the errors in the log and reports the analysis to a nurse, technician or other user at an institution. The harm index assessment module 504 may generate reports for a specified patient care device or may consolidate event reports from all, or a selected subset of, the patient care devices in an institution.

The harm index assessment module 504 works in concert with the medical administration management module 500 and event history module 502, utilizing the alert logs and other data collected by these modules to determine and report the level of harm associated with the various errors. For example, the medication administration management module 500 may receive, or retrieve, information from patient care devices related to alarms or alerts generated by the patient care device before or during administration of medical treatments to a patient. The harm index assessment module 504 may then analyze the information and provide reports related to harm assessment. When the patient care device 48 is not directly attached to a network, information relating to alerts may be uploaded to a hospital computer running modules 500 and 504 via a RS232 port or other connection. In this way, each patient care device's data may be individually uploaded and compiled into one or more databases of alert logs.

In those embodiments where the patient care device 48 automatically calculates a harm index value for averted errors, the harm index values may be transmitted with the other alert data. In such a case, the processor 72 or 82 of the patient care device 48 performs the data analysis to calculate the harm index values and the harm assessment module 504 provides compilation and reporting of the harm index values. Alternatively, harm index assessment of averted medication errors may be provided solely in retrospective fashion on aggregate medication error data using the pharmacy CPU 44, nursing CPU 46 or a processor associated with the hospital information system server 40 or another work station such as at the biomedical department. In this embodiment, data such as the maximum dosage limit and level of care specific to each particular error may be included in the alert logs retrieved from each patient care device.

The harm index assessment module generates reports of the overall harm index value of detected medication errors, such as that shown in FIG. 6. These reports may be used by the institution to improve the delivery of medication to patients in the institution, by identifying frequently occurring errors or conditions that can be corrected through improvements to the medication delivery process or training of caregivers. Such reports may either be customized on demand, that is, a caregiver or other individual responsible for analyzing the events may request a custom report, or the system may provide a menu of reporting formats pre-established by the institution that may be selected by the individual or department requesting the report. Alternatively, the system may be automated so that reports in pre-established formats are produced and distributed to appropriate individuals or departments in the institution at pre-selected intervals. The results of the analysis may also be stored in a memory for future use or distribution. The reports may be displayed on video displays 90 or 102 or may be printed on printer 100 or 106.

The features of the harm index assessment module 504 may alternatively be provided as part of another programming module such as the medical administration management module 500, rather than a separate module 504 as shown.

The clinical device tracking and reporting module 506 shown in FIG. 5 is used to maintain a record of the location of each clinical device and the history of its use in the institution. This system maintains a record of the current or last known location within the institution of each clinical device used in the institution, such as an infusion pump or vital sign sensor. Thus, the appropriate equipment can be easily located by a nurse or a technician for a given therapy regimen or vital sign measurement. This is particularly useful in a large hospital or clinic having many patient rooms, patient beds, or treatment areas where equipment may be temporarily misplaced. This system is also useful in those particular instances where an emergency occurs where treatment requires a particular piece of equipment. The status of that equipment can be easily ascertained from a remote video terminal, such as the video display 102 connected to the nursing CPU 46.

The clinical device tracking and reporting module 506 also maintains a record containing the usage history of each clinical device, including information about the patient it was used to treat, its location, the date, time, duration of use, any alarms that occurred and what medications were dispensed. This history may also contain the maintenance and calibration records for a clinical device. Such information can be queried on-line by technicians, nurses or other hospital administration personnel to generate reports to assist in locating the clinical device, report on the historical usage of the device, and to provide a log of preventative maintenance and equipment calibration. The efficient calibration of complex and sensitive clinical devices is particularly important in a heath care institution to maintain accuracy and quality of therapeutic treatment delivery. Maintaining a history of the usage of the device is also helpful to justify purchasing additional clinical devices when needed, or where the record indicates that a particular clinical device has become obsolete and needs to be replaced by a newer model of the device.

The information and care management system 28 also includes a consumable tracking module 508 that maintains a record of all consumable item usage for treatment of each patient. This record ensures that appropriate supplies are ordered and delivered to the nursing unit in a timely and cost-efficient manner to prevent outages of necessary supplies. Such information may also be used by the hospital inventory systems through an appropriate interface or other management system to ensure that the supply purchasing is done as cost-effectively as possible. The consumable tracking module 508 provides on-line queries and report generation summarizing consumable uses for a particular patient, a particular nursing unit, or a variety of other purposes.

The unit management tool module 510 assists nurses in sharing information related to patients and automates routine transactions within the nursing unit. The unit management tool module 510 allows a nurse to record the allergies, handicaps, and special care needs of the patient which, cooperating with the medical administration record module 500 and the clinical monitoring and event history module 502, displays that information prominently on all appropriate display screens, either at the pharmacy video display 90, the nursing video display 102 (FIG. 1) or at a bedside video display. The unit management tools module 510 also allows a nurse to record patient transfers and the times when the patient is out of the room or off the floor, such as, for example, when the patient is transferred to surgery or to a different part of the institution for a particular kind of treatment such as rehabilitative therapy. This system may also be programmed to signal an alarm when a patient has been disconnected from the system longer than scheduled, for example, when the patient disconnects from the infusion to attend to personal hygiene. This function ensures that an alarm or alert is sounded and that appropriate personnel are notified of any potential problems and can take the necessary actions to alleviate the alert condition.

The knowledge resource tools module 512 provides a framework for information sharing among the various units in the hospital and also supports an assortment of everyday tools used by the nurses, physicians and technicians involved in the delivery of health care within the institution. This module allows or assists in integrating external information sources into the care system 30 to improve the effectiveness of the care management team in treating the patients in the institution.

For example, the knowledge resource tools module 512 may provide a variety of on-line tools including, for example, a calculator, a dose rate calculator for calculating the appropriate dosage and infusion rate for a particular drug to be infused into a patient, a standard measurement conversion calculator for converting between units of measurement, a skin surface area calculator, and a timer and stopwatch. These resources may be displayed on the video displays 90, 102 at appropriate points within the system, and are available from any CPU either in the pharmacy, at the nursing station or at the bedside. These application tools can be programmed to appear on the video display 90, 102 either automatically, such as, for example, when an infusion pump is configured at the start of an infusion to assist in the calculation of a dose rate. These resources may also be available upon entry of the appropriate command by a nurse, physician or technician.

The information and care management system software can be written to operate on a variety of operating systems to suit the needs of a variety of institutions. In a present embodiment, the software is written to interface with the nurses and physicians using the Windows environment (Windows is a trademark of Microsoft, Inc.) on IBM compatible microcomputers. The Windows environment is well-known by those skilled in the art and will not be described in detail herein. The care management system software, when implemented using the Windows system, is particularly useful in that the Windows operating system provides the ability to load several programs at once. Multitasking programs, allowing several application programs to run simultaneously yet providing immediate access to the various software modules of the information and care management system 28 may also be used.

One particular mode of operation of the present invention will now be described. Most hospitals commonly have an established formulary of medications which defines how the medications are typically dispensed. When a patient care management system according to the present invention is first installed, a hospital committee may be formed to determine how that formulary would be applied to the patient care devices in the institution. The configuration definitions (e.g., by hospital unit such as ICU, NICU, Pediatrics, Oncology, Surgery, etc.) are agreed upon and the drugs and typical infusion protocols and guidelines are established. In addition, all out-of-limit conditions are defined. A technician at the institution may enter these values into the configuration databases 200, 202, 204 and 206, to customize it for the particular institution. Alternatively, an institution may purchase, or otherwise be provided, with a medical database, containing commonly used rule sets, protocols, out-of-limits events and the like, which may be used by the institution, or which may be modified by the institution as desired. Likewise, the harm index database 400 may be provided to an institution with harm index values already defined or the institution may customize its own harm index values.

A patient entering a hospital or other care giving facility is provided with a wristband, necklace, ankle band or other identifier that is affixed to the patient in a manner so that the patient can be identified even if the patient is unconscious or otherwise unresponsive. This wristband or other device may include a bar code representing the name of the patient and other information that the institute has determined is important. Additionally, any other information such as age, allergies, or other vital information may be encoded into the bar code. Alternatively, the patient information device may be an active embedded computer or passive device attached to a wrist band or other carrier that is attached to the patient. Such a device would be responsive to devices located throughout the care-giving facility, such as readers or wireless transmitter/receivers, to provide the identity of the patient along with other information when the device is queried.

After the patient is admitted and situated in a bed within the facility, the patient is typically evaluated by a physician and a course of treatment is prescribed. The physician prescribes a course of treatment by preparing an order which may request a series of laboratory tests or administration of a particular medication to the patient. In some cases, the physician prepares the order by filling in a form or writing the order on a slip of paper to be entered into the hospital system for providing care. In other cases, the physician may enter the medication order directly into a physician order entry system 38 (FIG. 1) or may instruct a nurse or other care-giving professional to do so.

If the order is for administration of a particular medication regimen, the order will be transmitted to the facility's pharmacy. The order will arrive in written or electronic form at the pharmacy, will be evaluated by the pharmacy, and processed. The pharmacy then prepares the medication according to the requirements of the physician. Typically, the pharmacy packages the medication in a container, and a copy of the order, or at a minimum the patient's name, the drug name, and the appropriate treatment parameters are represented on a label that is affixed to the drug container. This information may be represented by a bar code, or it may be stored in a smart label, such as a label having an embedded computer or passive device. The existence of this medication order is made available by the hospital's pharmacy information system 36 and may be stored by the server 40.

Generally, the medication is then delivered to the appropriate caregiving unit for administering to the patient. A nurse or technician carries the drug container to the appropriate patient. In accordance with one embodiment of the present invention, the nurse or technician first reads the barcode on the patient ID bracelet using the barcode reader 66 connected to the patient care device 48 or, alternatively, a bedside CPU. The nurse or technician would then read the barcode on the label affixed to the drug container by swiping the barcode wand across the barcode printed on the label of the drug container. Additionally, a record of the identity of the caregiver dispensing the medication may be obtained by reading the barcode printed on an identity badge typically worn by all institution personnel.

While the foregoing has been described with reference to the use of barcoded labels, those skilled in the art will also understand that passive identification devices such as those described above may be used to identify the patient, caregiver and medication to be administered. Such a system eliminates the need to read the barcodes and provides for relatively automatic identification and processing to determine if the right patient is being administered the right drug.

For certain drugs, the care-giver is prompted to enter data descriptive of a selected patient parameter or parameters, such a laboratory value or a current vital sign, before completing the verification process. For example, the care-giver may be prompted to measure and enter a value for a patient's blood pressure before administering certain selected drugs. At this time, the appropriate configuration database may also be selected and verified. The system may include medication administration guidelines including protocols are rule sets providing ranges of acceptable values for the parameters for the selected configuration database 204, as shown in FIG. 3. If the system detects an out-of-range value for the parameter, the harm index assessment system of the present invention assesses the severity of the error using harm index database 400 (FIGS. 4A-4C) and, based on a calculated overall harm index value, causes an appropriate alert to be provided. In an alternative embodiment, the parameters could be monitored and entered into the system automatically, eliminating the need for manual entry by the care-giver.

Once the medication delivery parameters and any other data is entered into the pump, the data is analyzed by the medical administration management module 500 which records the therapeutic regimen information in the patient's MAR, and verifies that the right medication is being given to the right patient in the right dose by the right route and at the right time. If the medical administration management module 500 detects a discrepancy between the barcoded information printed on the patient bracelet and the barcoded information on the label affixed to the medication container, the harm index assessment system may also be used to assess the error and provide an appropriate alert. The nurse or technician then either corrects the discrepancy by either re-reading the barcode on the patient's bracelet and the barcode on the medication container or, alternatively, by entering the appropriate information into the bedside CPU 80 using the keyboard 82 or touch screen 83, mouse, or other device. In the event that the nurse or technician determines that the discrepancy cannot be automatically corrected by re-reading the barcodes and that the harm index value indicates that the error is minimal and will not affect the accuracy or safety of the delivery of the medication, the nurse or technician may override the alert.

In an embodiment of the present invention, where the medication is to be delivered using an infusion pump, such as the infusion pump 52 attached to interface unit 50, the care management system automatically downloads information consisting of the appropriate configuration parameters for the infusion from the pharmacy CPU 44 through the communication system 30 into the interface unit 50 when the verification function of the medical administration management module 500 is complete. This is particularly advantageous in that one potential source of inaccuracy is eliminated by automatically configuring the pump, thus eliminating the need for the nurse or technician to manually enter the parameters necessary to configure the infusion pump 52. In an embodiment where the pumps cannot be automatically configured by downloading parameters from the network, the information and care management system 28 only verifies that the right treatment is being administered to the right patient. The pump must then be manually configured by the physician, nurse or technician.

Once the infusion pump or other patient care device is configured, the nurse, caregiver, or technician starts the infusion by pressing the appropriate control on the infusion pump 54. Starting a pump that is capable of being monitored automatically by the information and care management system causes a signal to be transmitted from the pump to the bedside CPU which is then logged by the clinical monitoring and event history module 502 and entered by the medical administration management module 500 into the patient's MAR. In the case where the institution is using a pump that is not capable of being configured by downloading parameters from the network, the nurse or other caregiver logs the start of the infusion using, for example, a bedside CPU, the nursing CPU 46 or a PDA. In this case, the video displays of the care management system that display information about the status of the infusion will not display real-time data. Rather, the care management system will project what the status of the infusion should be given the infusion parameters, the time elapsed since the infusion began, and any other events that were manually logged by the caregiver that may have affected the progress of the infusion.

The care management system, utilizing the application modules described above, monitors the infusion process in a real-time manner, providing alerts on the appropriate video display screens located throughout the institution and allows intervention by nurses or other caregivers at remote locations if necessary. In addition, the information and care management system of the present invention, utilizing harm index assessment module 504, provides retrospective analysis of the alert logs generated by the patient care devices. For example, harm index assessment module 504 provides reports to the care-giver or technician regarding the harm index values associated with various medication errors averted at the institution.

Furthermore, the institutional communication system 30 as mentioned above numerous times are not meant to be taken in a limited sense. Such a communication system may encompass an entire hospital facility or may be located only in a small area of the hospital. It may also include a communication system in a care-giving facility other than a hospital and may have application to an alternate care facility, such as a patient's home. The above embodiments are described for exemplary purposes only.

In the above detailed description, well-known devices, methods, procedures, and individual components have not been described in detail so as not to obscure aspects of the present invention. Those skilled in the art will understand those devices, methods, procedures, and individual components without further details being provided here. Moreover, while the embodiments disclosed above are described for use in a hospital environment, it will be understood that the system and method may be useful in other environments as well, such as outpatient clinics and other environments where care is delivered to a patient.

While several specific embodiments of the invention have been illustrated and described, it will be apparent that various modifications can be made without departing from the spirit and scope of the invention. Accordingly, it is not intended that the invention be limited, except as by the appended claims.

We claim:

1. A method for assessing potential for harm of detected medication errors associated with delivering medication to a patient, comprising the steps of:

receiving, via a user interface at a patient care device, entered medication administration parameter values that program the patient care device to deliver medication to a patient;

wherein the patient care device further includes a memory in which is stored medication administration guidelines representing acceptable values for the medication administration parameters;

comparing, via a processor at the patient care device, the entered medication administration parameter values to the acceptable medication administration parameter values stored in the memory, and further indicating medication errors whenever discrepancies between the values are detected;

storing, via the processor, a log of the detected medication errors in the memory;

wherein the memory further stores a harm index database including quantifiable harm index values representing a potential for harm associated with a plurality of potential medication errors;

wherein the harm index database further includes a plurality of harm index parameters relating to patient treatment, each harm index parameter being associated with the quantifiable harm index values;

wherein the harm index parameters further include an overdose parameter which further includes a drug type parameter associated with a dosage parameter, the drug type parameter indicates a potential for causing harm when the drug is incorrectly prescribed, and the dosage parameter indicates a potential for causing harm based on the magnitude of the drug dosage;

wherein the harm index parameters further include a level of care parameter which defines a risk for a given level of care;

wherein the harm index parameters further include a detectability parameter which defines the likelihood that the medication error would have been detected by a care-giver before a harmful adverse drug event occurs;

determining, via the processor, a quantifiable harm index value for each detected medication error stored in the log, and a quantifiable overall harm index value indicating the aggregate severity of the averted medication errors stored in the log based on combining the harm index values associated with the corresponding medication errors stored in the harm index database; and displaying, via a display at the patient care device, a report of the overall harm index value to the device user before potentially harmful medication delivery.

2. The method of claim 1, further comprising the steps of:
generating, via the display, an alert based on the severity of the overall harm index value by varying the loudness or pattern of an audible alarm or by varying a visual alarm.

3. The method of claim 2, wherein, based on the criticality of the error, the alert is provided either at the point of care, or at the point of care and a remote location.

4. The method of claim 1, wherein the drug type parameter is divided into categories that indicate low risk, medium risk, and high risk, and the dosage parameter is divided into categories indicate low risk, moderate risk, and high risk, and the cross association of the categories of the respective parameters yields a quantifiable harm index value.

5. The method of claim 1, wherein patient-specific information including laboratory results and age are included as factors integrated into the level or care parameter.

6. The method of claim 1, wherein the detectability parameter is divided into two categories, each associated with a harm index value, that indicate error detection would have either been likely or unlikely.

7. The method of claim 1, wherein the overall harm index value ranges from 3.5 to 14, with the low end of the range indicating a minimal harm potential, the middle of the range indicating a moderate harm potential, and the high end of the rage indicating a severe harm potential.

8. The method of claim 1, further comprising the steps of:
printing, via a printer operatively connected to the patient care device, a report including the overall harm index value.

9. A system for assessing potential for harm of detected medication errors associated with delivering medication to a patient, comprising:
a patient care device for delivering medication to a patient;
the patient care device including a user interface in which is entered medication administration parameter values that program the patient care device to deliver medication to a patient;
wherein the patient care device further includes a memory in which is stored medication administration guidelines representing acceptable values for the medication administration parameters;
the patient care device including a processor configured to compare the entered medication administration parameter values to the acceptable medication administration parameter values stored in the memory, and indicate medication errors whenever discrepancies between the values are detected;
the processor is further configured to store in the memory a log of the detected medication errors;
wherein the memory further stores a harm index database including quantifiable harm index values representing a potential for harm associated with a plurality of potential medication errors;
wherein the harm index database further includes a plurality of harm index parameters relating to patient treatment, each harm index parameter being associated with the quantifiable harm index values;
wherein the harm index parameters further include an overdose parameter which further includes a drug type parameter associated with a dosage parameter, the drug type parameter indicates a potential for causing harm when the drug is incorrectly prescribed, and the dosage parameter indicates a potential for causing harm based on the magnitude of the drug dosage;
wherein the harm index parameters further include a level of care parameter which defines a risk for a given level of care;
wherein the harm index parameters further include a detectability parameter which defines the likelihood that the medication error would have been detected by a care-giver before a harmful adverse drug event occurs;
the processor is further configured to determine a quantifiable harm index value for each detected medication error stored in the log, and a quantifiable overall harm index value indicating the aggregate severity of the averted medication errors stored in the log based on combining the harm index values associated with the corresponding medication errors stored in the harm index database; and
the patient care device including a display configured to report to the device user the overall harm index value before potentially harmful medication delivery.

10. The system of claim 9, wherein the patient care device generates an alert based on the severity of the overall harm index value by varying the loudness or pattern of an audible alarm or by varying the display of a visual alarm.

11. The system of claim 10, wherein, based on the criticality of the error, the alert is provided either at the point of care, or at the point of care and a remote location.

12. The system of claim 9, wherein the drug type parameter is divided into categories that indicate low risk, medium risk, and high risk, and the dosage parameter is divided into categories indicate low risk, moderate risk, and high risk, and the cross association of the categories of the respective parameters yields a quantifiable harm index value.

13. The system of claim 9, wherein patient-specific information including laboratory results and age are included as factors integrated into the level or care parameter.

14. The system of claim 9, wherein the detectability parameter is divided into two categories, each associated with a harm index value, that indicate error detection would have either been likely or unlikely.

15. The system of claim 9, wherein the overall harm index value ranges from 3.5 to 14, with the low end of the range indicating a minimal harm potential, the middle of the range indicating a moderate harm potential, and the high end of the rage indicating a severe harm potential.

16. The system of claim 9, wherein a printer is operatively connected to the patient care device and prints a report including the overall harm index value.

* * * * *